(12) United States Patent
Georgiades et al.

(10) Patent No.: US 8,168,585 B2
(45) Date of Patent: May 1, 2012

(54) PURIFICATION OF PEPTIDES FROM COLOSTRUM

(75) Inventors: Jerzy Alexander Georgiades, Houston, TX (US); Antoni Polanowski, Wroclaw (PL); Tadeusz Wilusz, Wroclaw (PL); Marian L. Kruzel, Houston, TX (US)

(73) Assignee: Regen Therapeutics PLC, London (GB)

( * ) Notice: Subject to any disclaimer, the term of this patent is extended or adjusted under 35 U.S.C. 154(b) by 109 days.

(21) Appl. No.: 12/436,584

(22) Filed: May 6, 2009

(65) Prior Publication Data

US 2009/0234099 A1 Sep. 17, 2009

Related U.S. Application Data

(63) Continuation of application No. 10/548,502, filed as application No. PCT/GB2004/001014 on Mar. 10, 2004, now abandoned.

(30) Foreign Application Priority Data

Mar. 11, 2003 (GB) ................................. 0305552.2
Mar. 8, 2004 (GB) ................................. 0405190.0

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. .......... 514/1.1; 530/328; 530/329; 530/330

(58) Field of Classification Search .................. None
See application file for complete search history.

(56) References Cited

U.S. PATENT DOCUMENTS

| 2,890,986 A | * | 6/1959 | Korbel et al. | ................. | 530/314 |
| 4,069,216 A | * | 1/1978 | Shanbrom | ..................... | 530/383 |
| 4,104,125 A | * | 8/1978 | Takechi et al. | ................. | 435/206 |
| 4,368,262 A | * | 1/1983 | Bucovaz et al. | ................. | 435/23 |
| 4,816,563 A | * | 3/1989 | Wilson et al. | ................. | 530/344 |
| 6,093,693 A | | 7/2000 | Julius et al. | | |
| 6,852,685 B1 | * | 2/2005 | Boldogh et al. | ................. | 514/8.3 |

FOREIGN PATENT DOCUMENTS

| FR | 2617049 | 12/1988 |
| JP | 2001240599 | 9/2001 |
| WO | 98/14473 | 4/1998 |

OTHER PUBLICATIONS

Yamamoto et al. Purification and Properties of Biologically Active Chromium Complex from Bovine Colostrum. J Nutr. 1988, vol. 118, pp. 39-45.*

Janusz, M. et al.; "Chemical and physical characterization of a proline-rich polypeptide from sheep colostrum"; Biochemical Journal; Portland Press; London, Great Britain; vol. 199; 1981; pp. 9-15; XP002938312.

Amarant, Tanchum et al; Luteinzing Hormone-Releasing Hormone and Thyrotrophin-Releasing Hormone in Human and Bovine Milk; Department of Organic Chemistry and Hormone Research, The Weizman Institute of Science. 127, pp. 647-650.

New Biochemical Experiment Course 9; First Print, First Edition, Data Published Jun. 20, 1991; Hormone I; -Peptide Hormone-; 1991; Edited by The Japanese Biochemical Society; Published by Atsushi Ueki; Publisher Tokyo Kagaku-Dojin Publishing Co., Inc.

New Biochemical Experiment Course 1; First Print, First Edition, Data Published Feb. 26, 1990; Protein I; -Separation, Purification, Property-; 1991; Edited by The Japanese Biochemical Society; Published by Atsushi Ueki; Publisher Tokyo Kagaku-Dojin Publishing Co., Inc.

Kruzel, ML et al.; "The Alcohol-Induced Conformational Changes in Casein Micelles: A New Challenge for the Purification of Colostrinin"; The Protein Journal; vol. 23, No. 2; Feb. 2, 2004; pp. 127-133; XP008031778.

Linn, Methods in Enzymology, 1990, vol. 182, pp. 9-15.

* cited by examiner

*Primary Examiner* — Marcela M Cordero Garcia
(74) *Attorney, Agent, or Firm* — Rankin, Hill & Clark LLP (57) ABSTRACT

The invention relates to the purification of peptides from colostrum. The method involves the addition of an alcohol such as methanol or ethanol to the mixture in order to form an alcohol phase rich in the peptides, and a precipitate. The peptide-rich alcohol phase is subsequently recovered and subjected to further fractionation. The invention is particularly useful in the purification of colostrinin from colostrum.

18 Claims, 2 Drawing Sheets

Fig.2.

SEQUENCE LISTING

<160> NUMBER OF SEQ ID NOS: 64

<210> SEQ ID NO 1
<211> LENGTH: 17
<212> TYPE: PRT
<213> ORGANISM: Ovis aries

<400> SEQUENCE: 1

Leu Gln Thr Pro Gln Pro Leu Leu Gln Val Met Met Glu Pro Gln Gly
1               5                   10                  15

Asp

<210> SEQ ID NO 2
<211> LENGTH: 11
<212> TYPE: PRT
<213> ORGANISM: Ovis aries

<400> SEQUENCE: 2

Met Pro Gln Asn Phe Tyr Lys Leu Pro Gln Met
1               5                   10

<210> SEQ ID NO 3
<211> LENGTH: 15
<212> TYPE: PRT
<213> ORGANISM: Ovis aries

<400> SEQUENCE: 3

Val Leu Glu Met Lys Phe Pro Pro Pro Gln Glu Thr Val Thr
1               5                   10                  15

<210> SEQ ID NO 4
<211> LENGTH: 15
<212> TYPE: PRT
<213> ORGANISM: Ovis aries

<400> SEQUENCE: 4

Leu Lys Pro Phe Pro Lys Leu Lys Val Glu Val Phe Pro Phe Pro
1               5                   10                  15

<210> SEQ ID NO 5
<211> LENGTH: 4
<212> TYPE: PRT
<213> ORGANISM: Ovis aries

<400> SEQUENCE: 5

Ser Glu Gln Pro
1

<210> SEQ ID NO 6
<211> LENGTH: 3
<212> TYPE: PRT
<213> ORGANISM: Ovis aries

<400> SEQUENCE: 6

Asp Lys Glu
1

<210> SEQ ID NO 7
<211> LENGTH: 7
<212> TYPE: PRT
<213> ORGANISM: Ovis aries

<400> SEQUENCE: 7

```
Asp Pro Pro Pro Gln Ser
1               5

<210> SEQ ID NO 8
<211> LENGTH: 3
<212> TYPE: PRT
<213> ORGANISM: Ovis aries

<400> SEQUENCE: 8

Leu Asn Phe
1

<210> SEQ ID NO 9
<211> LENGTH: 7
<212> TYPE: PRT
<213> ORGANISM: Ovis aries

<400> SEQUENCE: 9

Val Leu Pro Pro Asn Val Gly
1               5

<210> SEQ ID NO 10
<211> LENGTH: 7
<212> TYPE: PRT
<213> ORGANISM: Ovis aries

<400> SEQUENCE: 10

Lys Tyr Lys Leu Gln Pro Glu
1               5

<210> SEQ ID NO 11
<211> LENGTH: 5
<212> TYPE: PRT
<213> ORGANISM: Ovis aries

<400> SEQUENCE: 11

Ser Glu Glu Met Pro
1               5

<210> SEQ ID NO 12
<211> LENGTH: 6
<212> TYPE: PRT
<213> ORGANISM: Ovis aries

<400> SEQUENCE: 12

Asp Ser Gln Pro Pro Val
1               5

<210> SEQ ID NO 13
<211> LENGTH: 5
<212> TYPE: PRT
<213> ORGANISM: Ovis aries

<400> SEQUENCE: 13

Phe Pro Pro Pro Lys
1               5

<210> SEQ ID NO 14
<211> LENGTH: 5
<212> TYPE: PRT
<213> ORGANISM: Ovis aries

<400> SEQUENCE: 14

Val Val Met Glu Val
1               5
```

-continued

<210> SEQ ID NO 15
<211> LENGTH: 15
<212> TYPE: PRT
<213> ORGANISM: Ovis aries

<400> SEQUENCE: 15

Asp Leu Glu Met Pro Val Leu Pro Val Glu Pro Phe Pro Phe Val
1               5                   10                  15

<210> SEQ ID NO 16
<211> LENGTH: 12
<212> TYPE: PRT
<213> ORGANISM: Ovis aries

<400> SEQUENCE: 16

Leu Phe Phe Phe Leu Pro Val Val Asn Val Leu Pro
1               5                   10

<210> SEQ ID NO 17
<211> LENGTH: 7
<212> TYPE: PRT
<213> ORGANISM: Ovis aries

<400> SEQUENCE: 17

Met Gln Pro Pro Pro Leu Pro
1               5

<210> SEQ ID NO 18
<211> LENGTH: 18
<212> TYPE: PRT
<213> ORGANISM: Ovis aries

<400> SEQUENCE: 18

Asp Gln Pro Pro Asp Val Glu Lys Pro Asp Leu Gln Pro Phe Gln Val
1               5                   10                  15

Gln Ser

<210> SEQ ID NO 19
<211> LENGTH: 10
<212> TYPE: PRT
<213> ORGANISM: Ovis aries

<400> SEQUENCE: 19

Val Tyr Pro Phe Thr Gly Pro Ile Pro Asn
1               5                   10

<210> SEQ ID NO 20
<211> LENGTH: 9
<212> TYPE: PRT
<213> ORGANISM: Ovis aries

<400> SEQUENCE: 20

Ser Leu Pro Gln Asn Ile Leu Pro Leu
1               5

<210> SEQ ID NO 21
<211> LENGTH: 10
<212> TYPE: PRT
<213> ORGANISM: Ovis aries

<400> SEQUENCE: 21

Thr Gln Thr Pro Val Val Val Pro Pro Phe
1               5                   10

```
<210> SEQ ID NO 22
<211> LENGTH: 18
<212> TYPE: PRT
<213> ORGANISM: Ovis aries

<400> SEQUENCE: 22

Leu Gln Pro Glu Ile Met Gly Val Pro Lys Val Lys Glu Thr Met Val
1               5                   10                  15

Pro Lys

<210> SEQ ID NO 23
<211> LENGTH: 18
<212> TYPE: PRT
<213> ORGANISM: Ovis aries

<400> SEQUENCE: 23

His Lys Glu Met Pro Phe Pro Lys Tyr Pro Val Glu Pro Phe Thr Glu
1               5                   10                  15

Ser Gln

<210> SEQ ID NO 24
<211> LENGTH: 18
<212> TYPE: PRT
<213> ORGANISM: Ovis aries

<400> SEQUENCE: 24

Ser Leu Thr Leu Thr Asp Val Glu Lys Leu His Leu Pro Leu Pro Leu
1               5                   10                  15

Val Gln

<210> SEQ ID NO 25
<211> LENGTH: 7
<212> TYPE: PRT
<213> ORGANISM: Ovis aries

<400> SEQUENCE: 25

Ser Trp Met His Gln Pro Pro
1               5

<210> SEQ ID NO 26
<211> LENGTH: 10
<212> TYPE: PRT
<213> ORGANISM: Ovis aries

<400> SEQUENCE: 26

Gln Pro Leu Pro Pro Thr Val Met Phe Pro
1               5                   10

<210> SEQ ID NO 27
<211> LENGTH: 15
<212> TYPE: PRT
<213> ORGANISM: Ovis aries

<400> SEQUENCE: 27

Met His Gln Pro Pro Gln Pro Leu Pro Pro Thr Val Met Phe Pro
1               5                   10                  15

<210> SEQ ID NO 28
<211> LENGTH: 6
<212> TYPE: PRT
<213> ORGANISM: Ovis aries

<400> SEQUENCE: 28

Pro Gln Ser Val Leu Ser
```

```
<210> SEQ ID NO 29
<211> LENGTH: 22
<212> TYPE: PRT
<213> ORGANISM: Ovis aries

<400> SEQUENCE: 29

Leu Ser Gln Pro Lys Val Leu Pro Val Pro Gln Lys Ala Val Pro Gln
1               5                   10                  15

Arg Asp Met Pro Ile Gln
            20

<210> SEQ ID NO 30
<211> LENGTH: 7
<212> TYPE: PRT
<213> ORGANISM: Ovis aries

<400> SEQUENCE: 30

Ala Phe Leu Leu Tyr Gln Glu
1               5

<210> SEQ ID NO 31
<211> LENGTH: 13
<212> TYPE: PRT
<213> ORGANISM: Ovis aries

<400> SEQUENCE: 31

Phe Leu Leu Tyr Gln Glu Pro Val Leu Gly Pro Val Arg
1               5                   10

<210> SEQ ID NO 32
<211> LENGTH: 8
<212> TYPE: PRT
<213> ORGANISM: Ovis aries

<400> SEQUENCE: 32

Arg Gly Pro Phe Pro Ile Leu Val
1               5

<210> SEQ ID NO 33
<211> LENGTH: 18
<212> TYPE: PRT
<213> ORGANISM: Ovis aries

<400> SEQUENCE: 33

Ala Thr Phe Asn Arg Tyr Gln Asp Asp His Gly Glu Glu Ile Leu Lys
1               5                   10                  15

Ser Leu

<210> SEQ ID NO 34
<211> LENGTH: 19
<212> TYPE: PRT
<213> ORGANISM: Ovis aries

<400> SEQUENCE: 34

Leu Val Tyr Pro Phe Thr Gly Pro Ile Pro Asn Ser Leu Pro Gln Asn
1               5                   10                  15

Ile Leu Pro

<210> SEQ ID NO 35
<211> LENGTH: 13
<212> TYPE: PRT
<213> ORGANISM: Ovis aries
```

<400> SEQUENCE: 35

Met Ile Val Val Arg Leu Leu Gln Asn Glu Val Pro Glu
1               5                   10

<210> SEQ ID NO 36
<211> LENGTH: 10
<212> TYPE: PRT
<213> ORGANISM: Ovis aries

<400> SEQUENCE: 36

Ser Leu Ser Gln Ser Lys Val Leu Pro Val
1               5                   10

<210> SEQ ID NO 37
<211> LENGTH: 8
<212> TYPE: PRT
<213> ORGANISM: Ovis aries

<400> SEQUENCE: 37

Leu Gln Thr Gln Thr Pro Val Val
1               5

<210> SEQ ID NO 38
<211> LENGTH: 7
<212> TYPE: PRT
<213> ORGANISM: Ovis aries

<400> SEQUENCE: 38

Glu Met Pro Phe Pro Lys Tyr
1               5

<210> SEQ ID NO 39
<211> LENGTH: 6
<212> TYPE: PRT
<213> ORGANISM: Ovis aries

<400> SEQUENCE: 39

Pro Val Glu Pro Phe Thr
1               5

<210> SEQ ID NO 40
<211> LENGTH: 6
<212> TYPE: PRT
<213> ORGANISM: Ovis aries

<400> SEQUENCE: 40

Val Pro Pro Phe Leu Gln
1               5

<210> SEQ ID NO 41
<211> LENGTH: 5
<212> TYPE: PRT
<213> ORGANISM: Ovis aries

<400> SEQUENCE: 41

Pro Met Phe Leu Gln
1               5

<210> SEQ ID NO 42
<211> LENGTH: 5
<212> TYPE: PRT
<213> ORGANISM: Ovis aries

<400> SEQUENCE: 42

```
Glu His Met Phe Val
1               5

<210> SEQ ID NO 43
<211> LENGTH: 4
<212> TYPE: PRT
<213> ORGANISM: Ovis aries

<400> SEQUENCE: 43

Thr Asp Arg Asp
1

<210> SEQ ID NO 44
<211> LENGTH: 4
<212> TYPE: PRT
<213> ORGANISM: Ovis aries

<400> SEQUENCE: 44

Val Gln Pro Thr
1

<210> SEQ ID NO 45
<211> LENGTH: 4
<212> TYPE: PRT
<213> ORGANISM: Ovis aries

<400> SEQUENCE: 45

Pro Lys Val Lys
1

<210> SEQ ID NO 46
<211> LENGTH: 4
<212> TYPE: PRT
<213> ORGANISM: Ovis aries

<400> SEQUENCE: 46

Asp Asp Asp Glu
1

<210> SEQ ID NO 47
<211> LENGTH: 4
<212> TYPE: PRT
<213> ORGANISM: Ovis aries

<400> SEQUENCE: 47

Thr Glu Glu Val
1

<210> SEQ ID NO 48
<211> LENGTH: 4
<212> TYPE: PRT
<213> ORGANISM: Ovis aries

<400> SEQUENCE: 48

Tyr Gln Gln Glu
1

<210> SEQ ID NO 49
<211> LENGTH: 4
<212> TYPE: PRT
<213> ORGANISM: Ovis aries

<400> SEQUENCE: 49

Phe Pro Pro Gln
1
```

-continued

```
<210> SEQ ID NO 50
<211> LENGTH: 4
<212> TYPE: PRT
<213> ORGANISM: Ovis aries

<400> SEQUENCE: 50

Gly Phe Gly Ile
1

<210> SEQ ID NO 51
<211> LENGTH: 3
<212> TYPE: PRT
<213> ORGANISM: Ovis aries

<400> SEQUENCE: 51

Leu Gln Ser
1

<210> SEQ ID NO 52
<211> LENGTH: 3
<212> TYPE: PRT
<213> ORGANISM: Ovis aries

<400> SEQUENCE: 52

Val Val Val
1

<210> SEQ ID NO 53
<211> LENGTH: 3
<212> TYPE: PRT
<213> ORGANISM: Ovis aries

<400> SEQUENCE: 53

Gly Gly Lys
1

<210> SEQ ID NO 54
<211> LENGTH: 3
<212> TYPE: PRT
<213> ORGANISM: Ovis aries

<400> SEQUENCE: 54

Asp Met Val
1

<210> SEQ ID NO 55
<211> LENGTH: 3
<212> TYPE: PRT
<213> ORGANISM: Ovis aries

<400> SEQUENCE: 55

Glu Ser Gln
1

<210> SEQ ID NO 56
<211> LENGTH: 3
<212> TYPE: PRT
<213> ORGANISM: Ovis aries

<400> SEQUENCE: 56

Gly Arg Val
1

<210> SEQ ID NO 57
<211> LENGTH: 3
```

```
<212> TYPE: PRT
<213> ORGANISM: Ovis aries

<400> SEQUENCE: 57

Val Glu Glu
1

<210> SEQ ID NO 58
<211> LENGTH: 3
<212> TYPE: PRT
<213> ORGANISM: Ovis aries

<400> SEQUENCE: 58

Ile Gly Asn
1

<210> SEQ ID NO 59
<211> LENGTH: 3
<212> TYPE: PRT
<213> ORGANISM: Ovis aries

<400> SEQUENCE: 59

Phe Phe Gln
1

<210> SEQ ID NO 60
<211> LENGTH: 3
<212> TYPE: PRT
<213> ORGANISM: Ovis aries

<400> SEQUENCE: 60

Arg Met Phe
1

<210> SEQ ID NO 61
<211> LENGTH: 3
<212> TYPE: PRT
<213> ORGANISM: Ovis aries

<400> SEQUENCE: 61

Phe Pro Pro
1

<210> SEQ ID NO 62
<211> LENGTH: 3
<212> TYPE: PRT
<213> ORGANISM: Ovis aries

<400> SEQUENCE: 62

Met His His
1

<210> SEQ ID NO 63
<211> LENGTH: 3
<212> TYPE: PRT
<213> ORGANISM: Ovis aries

<400> SEQUENCE: 63

Asn Thr Glu
1

<210> SEQ ID NO 64
<211> LENGTH: 9
<212> TYPE: PRT
<213> ORGANISM: Ovis aries
```

-continued

```
<400> SEQUENCE: 64

Val Glu Ser Tyr Val Pro Leu Phe Pro
1               5
```

PURIFICATION OF PEPTIDES FROM COLOSTRUM

CROSS-REFERENCE TO RELATED APPLICATIONS

The present application is a continuation of U.S. application Ser. No. 10/548,502, now abandoned, filed Aug. 14, 2006, which is a U.S. national stage of International Application PCT/GB2004/001014, filed Mar. 10, 2004, and claims priority to GB 0305552.2, filed Mar. 11, 2003, and GB 0405190.0, filed Mar. 8, 2004. The application includes a sequence listing, which is hereby incorporated by reference, that complies with the American Standard Code for Information Interchange (ASCII) and can be viewed using an IBM-PC compatible computer using the MS-Windows operating system.

BACKGROUND OF THE INVENTION

1. Field of Invention

This application relates to the purification of peptides from colostrum. The invention is particularly concerned with the purification of colostrinine from colostrum.

2. Description of Related Art

Colostrum, or foremilk, is a viscous mammary gland secretion characterized by the presence of many elements needed by newborn mammals to develop properly. It is the first lacteal secretion post parturition and contains a high concentration of immunoglobulins (IgG, IgM and IgA) and non-specific proteins. It is replaced by mature breast milk about four to five days after birth. Compared with mature breast milk, colostrum has low sugar content, but is richer in lipids, proteins, mineral salts and immunoglobulins. It also contains various floating cells such as granular and stromal cells, neutrophils, monocyte/macrophages and lymphocytes. It is also rich in growth factors, hormones and cytokines.

Amongst the proteins present in colostrum, caseins are the most prevalent and known to form aggregates (micelles), which are similar in all mammals. Many proteins and peptides are bound to those aggregates, by weak hydrophobic and ionic forces. The resultant network of proteinaceous micelles has the ability to trap many small molecular weight compounds of differing nature, such as lipids, carbohydrates, and peptides, forming a unique homogeneous solution. The micelles help to distribute these micro-molecules relatively uniformly throughout the colostrum, and also prevent them from the formation of unwanted aggregates.

A number of peptides from milk with various biological activities have been reported. Some peptides exist naturally and some can be released via enzymatic proteolysis of the parent milk proteins. Of particular interest are those naturally existing peptides that are bound to casein micelles. Besides casein protein, calcium and phosphate, the micelle also contains citrate, minor ions, lipase and plasmin enzymes, and various peptides entrapped in their structure. Therefore, the downstream purification processing of many milk-derived components recently become the most challenging effort for the dairy industry.

In general, the downstream processing of milk starts by coagulating caseins with addition of chymosin to give curds, which are then separated from the liquid, whey, after which they can be processed and matured to produce a variety of cheeses. Chymosin brakes down the kappa-casein molecules causing a global collapse of casein micelles. As a result many components of a soluble fraction of milk become entrapped in the precipitate and disregarded. Particularly small molecular peptides with a high hydrophobic index, such as colostrinine, can be lost.

The original purification protocol for obtaining colostrinine (Janusz et al.), consists of pH-dependent casein precipitation followed by various chromatographic steps, including ion exchange, affinity and molecular sieving, combined with ammonium sulfate precipitation. Although, this method is reproducible, it is laborious and difficult to scale-up for the industrial applications. Since then numerous protocols, utilizing membrane filtration, have been developed for recovery of low molecular weight peptides from milk and colostrum, but all of these have had shortcomings.

Tangential flow filtration is used in one standard protocol for separating milk components in the dairy industry. For example, in the U.S. Pat. No. 6,268,487 entitled Purification of Biologically Active Peptides from Milk by Kutzko et al., a method for separation of milk components by tangential flow filtration is disclosed. Also, an ultrafiltration is proposed by Roger et al., in a U.S. Pat. No. 4,485,040, entitled: Process for Obtaining an α-Lactalbumin Enriched Product from Whey, and Uses Thereof, to separate milk components on a membrane having cut-off greater than 5,000 (e.g. 50,000) at a pH between 6.3 and 7 (e.g. 6.6) and a temperature between 30° C. and 60° C.

The use of ultrafiltration is also described in U.S. Pat. No. 4,816,563 Wilson et al., entitled: Process for Obtaining Transfer Factor from Colostrum, Transfer Factor so Obtained and Use Thereof. In fact, filtration of milk or colostrum is a standard procedure in the dairy industry today. Wilson et al., describes the use of an agent to prepare a transfer factor from colostrum. Suitable agents are said to include alcohols, ketones and polyethylene glycol. There is, however, no description of the recovery of colostrinine from colostrum.

U.S. Pat. No. 5,216,129 discloses a process for obtaining kappa-caseino-glycomacropeptide from a whey product concentrated in proteins. The process involves the use of ethanol at a concentration of 5% to 25% based on the volume of the solution. The whey product is not colostrinine.

UK Patent 1,438,008 discloses a process for the extraction of a specific octapeptide from frog skin using alcohol.

JP520062796 discloses a method of extracting cyclic peptides from the root of Ribia akane Nakai using, inter alia, an alcohol.

In J Pharm Pharmaceut Sci, Vol 5, 2002. MEC Lutsiak et al., "Analysis of peptide and lipopeptide content in liposomes", p 279-284, there is disclosed a method for extracting peptides from liposomes.

In Journal of Antibiotics, Vol XL, 1987, E Meyers et al, "Xylocandin: a new complex of ant/fungal peptides I. Taxonomy, isolation and biological activity", p 1515-1519, there is disclosed method of extracting peptides from the bacteria *pseudomonas cepacia*.

In Acta Endocrinologica, vol 111, 1986, WF Blum et al, "Isolation and partial characterisation of six somatomedin-like peptides from human plasma Cohn fraction IV", p 271-284, there is disclosed the extraction of somatomedin-like peptides from human plasma using ethanol.

In J Dairy Research, vol 54, 1987, DS Horne, "Ethanol stability of Casein micelles—a hypothesis concerning the role of calcium phosphate", p 389-395, there is disclosed a hypothetical elaboration on casein micelles structure and calcium release.

In Ir. J. Fd. Sci. Techno!., vol 9, 1985, M M Hewedi et al, "Recovery of milk protein by ethanol precipitation", p 11-13, there is disclosed a method of precipitating milk proteins using ethanol.

COLOSTRININ®, also known as colostrinine, proline-rich polypeptide or PRP, was first isolated in 1974 (Janusz et al, FEBS Lett., 49, 276-279) from ovine colostrum. Certain therapeutic uses of COLOSTRININ®, particularly in the treatment of Alzheimer's disease, were described in WO98/14473, the contents of which are incorporated herein by reference. In this patent application, the physical characteristics of colostrinine, as deter inable at the time, were described. Although the physical characteristics were correct, the understanding of colostrinine has moved on since this application was filed. WO98/14473 also described a method for extracting colostrinine from raw colostrum, which is often referred to as the "Janusz" method. This method is presently the principle method of extracting colostrinine from colostrum. It has the disadvantages that the industrial scale up is difficult to obtain and yields from the method are low.

WO00/75173, the contents of which are incorporated herein by reference, describes a number of peptides found in colostrinine. WO02/46211, the contents of which are incorporated herein by reference, describes a number of other peptides which can be found in colostrinine.

Of considerable interest in colostrinine is the presence of various polypeptides that can be isolated only from colostrum, not mature milk. During the days following parturition, the concentration of colostrinine in a mammary gland secretion precipitously diminishes through the end of the third day after delivery. Such a short lifetime for some of the colostrinine peptides indicates their important role in early development of infant's immune system and the protection of newborns against environmental shocks.

Colostrinine has more recently been discovered to exist in two forms; free and aggregated (bound). It is thought that free forms of colostrinine are required to protect the newborn mammal from oxidative stress, which appears immediately after birth. The bound or aggregated forms are designed to maintain this function for prolonged periods of time after birth. The bound form of colostrinine, in addition, is thought to participate in the development and/or protection of different organs and systems. This takes place when oxidative stress problems subside, and free colostrinine concentrations begin to decrease. The bound form of colostrinine is slowly released into the body fluids to modulate physiological functions when the free form is exhausted. This model finds support in studies on the gradual disappearance of specific colostrinine peptides from colostrum after parturition.

The colostrinine complex is now believed to consist of at least five subgroups of peptides; each subgroup has its own characteristic hydrophobic pattern. Evidence suggests that these peptides have a tendency to form aggregates, due to the presence of specially arranged non-polar, polar, aromatic, positively- and negatively-charged amino acids. Furthermore, the amino acid compositions of the peptides and their hydrophobic character further suggest this aggregating ability.

From the presently available information, we have found that colostrinine peptides have the best biological activity when they are present in their native form. When they are purified, they start to interact with each other forming non-covalently bound complexes with apparently weaker biological activities. It is believed that colostrinine is a mixture of more than 62 separate peptides, derived from precursor proteins, such as annexin, beta-casein, a hypothetical beta-casein homologue and others with no homology to any specific protein in the current GenBank database.

BRIEF SUMMARY OF THE INVENTION

It is an object of the invention to develop a new method for extracting and recovering peptides from fluids containing higher molecular weight materials. It is a specific object of the invention to develop a method of purifying colostrinine from raw colostrum, so that the colostrinine can be produced in high yield in a form in which it will be biologically active and substantially pure. The purification method should yield the majority of the colostrinine peptides, both free and bound or aggregated. Purified colostrinine, free of contaminants and self-aggregates, will have more active principles per unit weight. A further object of the invention is to develop a purification protocol that will provide a consistent set of peptides characterized by specific biological activities.

This invention is based on the unexpected discovery that a simple extraction method can used to extract colostrinine at a high degree of purity from colostrum.

According to one aspect of the invention there is provided a method for recovering peptides from mammalian colostrum said method comprising: mixing the colostrum with an alcohol to form an alcohol phase and a precipitate, the alcohol phase including the alcohol and at least some of the peptides to be recovered; separating the alcohol phase from the precipitate; and recovering the alcohol phase.

The invention is particularly applicable to the purification of colostrinine from colostrum, and the following description is largely directed to this specific application.

BRIEF DESCRIPTION OF THE DRAWINGS

Reference is now made to the accompanying drawings, in which.

DETAILED DESCRIPTION OF THE INVENTION

The alcohol may be any alcohol capable of forming an alcohol phase containing colostrinine peptides when mixed with colostrum, and capable of precipitating unwanted higher molecular weight materials.

The alcohol may be linear or branched, and may contain one or more hydroxyl groups; one hydroxyl group is preferred. Preferably, the alcohol contains 1 to 5 carbon atoms, more preferably 1 to 4 carbon atoms, most preferably 1 to 3 carbon atoms. We have found that the best results are obtained with methanol or ethanol.

The alcohol is desirably added to the colostrum in a concentrated form: preferably the alcohol is at least 80% pure, more preferably at least 95% pure, and most preferably substantially 100% pure.

The amount of alcohol added to the colostrum is preferably such as to provide an alcohol concentration in the total composition of 40% (v/v) to 80% (v/v), more preferably 50% (v/v) to 70% (v/v), still more preferably 55% (v/v) to 65% (v/v) and most preferably substantially 60% (v/v).

The step of mixing the alcohol with the raw colostrum (which is known as "extraction"), is preferably carried out with stirring at room temperature for 10 to 30 minutes. This forms a precipitate containing the caseins and other proteins, while the colostrinine remains in solution in the alcohol phase. It is an important, and unexpected, feature of the invention that the colostrinine peptides substantially all remain in solution in the alcohol, while the other components of the colostrum are precipitated.

The precipitate may then be separated from the alcohol phase by any conventional means, preferably by centrifugation at about 15,000 g, and the alcohol phase containing the colostrum is recovered. The colostrinine is then separated from the alcohol, preferably by evaporation, to form a colostrinine-rich phase (which is largely an aqueous solution of colostrinine) which is recovered.

The step of separating the alcohol from the colostrinine peptides can be carried out by evaporation or extensive ultrafiltration, combined with water or buffer exchange, but the evaporation is preferred. The evaporation can be carried out at a temperature typically in the range of 10° C. to 50° C. A temperature of about 30° C. is preferred. The evaporation or filtration may be carried out over a time period of, for example, 30 minutes to 12 hours or more (e.g. overnight). Although the ultrafiltration is a viable option, the recovery is higher with evaporation. It may be desirable to eliminate alcohol by evaporation in a vacuum. After removal of the alcohol, sufficient water may be added to the colostrinine-rich phase to bring-up the volume of working solution to about initial volume.

In a preferred embodiment, the precipitate from the alcohol-extraction step is subsequently washed with a further quantity of alcohol, and the alcohol phase is again separated and recovered. This second recovered alcohol phase may contain some colostrinine peptides which were carried into the precipitate in the first extraction. The second recovered alcohol phase may be added directly to the alcohol phase recovered from the first extraction, or some or all of the alcohol may be removed first. After the alcohol has been removed, the remnants could be added directly to the colostrinine-rich phase.

Optionally, following removal of the alcohol, a further centrifugation step may be performed in order to separate any precipitate formed during the alcohol removal from the remaining solubilized fraction.

In a particularly advantageous embodiment of the invention, a precipitation agent is added either to the alcohol phase, or, preferably, to the colostrinine-rich phase (preferably after any additional centrifugation step). The purpose of the precipitation agent is to induce precipitation of the colostrinine peptides. We have found that ammonium sulfate is particularly suitable as the precipitation agent, but other materials which can fulfil the same purpose could be used instead, or in addition. The most effective precipitation agents are salts with multiple charged anions such as sulphate, phosphate, and citrate. As far as cations are concerned, monovalent ions should be used with $NH_4^+$ being preferred to $K^+$, and $K^+$ being preferred to $Na^+$. Typical precipitation agents are sodium, potassium and ammonium sulphates, phosphates and citrates, but ammonium sulphate is most preferred. The precipitation agent may instead be an organic polymer, such as polyethylene glycol. Precipitation with a precipitation agent further lowers the casein contamination and further purifies the colostrinine peptide fraction, enabling the formation of a consistent pool of essentially IgG-free peptides to be isolated in approximately two days. This process makes possible the rapid isolation of colostrinine peptides.

The precipitation agent is desirably added in an amount suitable to provide 30% (w/v) to 80% (w/v) saturation, preferably 40% (w/v) to 60% (w/v) saturation, and most preferably substantially 50% (w/v) saturation. The saturation percentages refer to saturation of the precipitation agent, such as ammonium sulfate, in liquid. The precipitation agent is preferably added as a saturated solution (i.e. 100% (w/v) saturation) in water.

However, the precipitation agent may also be added in crystalline form, in small amounts, followed by a vigorous stirring to avoid local saturation, for about 30 minutes for example, after each addition. This may be continued until the entire precipitation agent has been dissolved. This technique may take several hours, therefore is less preferred.

The addition of the precipitation agent causes the colostrinine peptides to be precipitated from the solution. When the addition is complete, the mixture is preferably left for a period of time, typically 30 minutes, possibly with stirring, or, preferably, with rocking.

At this stage, the mixture comprises an aqueous liquid phase and a precipitate. The liquid phase contains the precipitation agent dissolved therein, and, possibly, some of the higher molecular weight material which was not precipitated during the alcohol extraction step. The precipitate contains colostrinine peptides. The liquid phase is subsequently separated from the precipitate, preferably by centrifugation at about 15,000 g centrifugal force, and the precipitate is recovered.

The recovered precipitate is preferably dissolved in water, using the minimum amount of water necessary, followed by dialyzing, typically in 0.01 M PBS (phosphate buffered saline) or water. The dialysis step is carried out to remove excess ions, although some ions of the precipitation agent ions may remain. The dialysed solution may then be clarified by centrifugation, then lyophilized. The final material contains separated colostrinine peptides, which may be stored at −20° C. for future use in the preparation of a pharmaceutical, nutraceutical and other compositions. These may be made by conventional means.

Various quality control tests may be carried out, to ensure that the final material is suitable for use in the preparation of a medicament. Such tests are known to those skilled in the art, but may involve SDS PAGE; isoefectrofocusing profile; amino acid analysis; determining the antigenic composition of colostrinine by means of the ELISA method using monospecific antibodies; determining the capability to induce cytokines such as interferon gamma (IFN-γ); tumour necrosis factor (TNF) and determining the antioxidant properties. The final material should not contain any high molecular weight proteins. If the quality control tests indicate the presence of impurities, the final material may need to be further purified. There are several methods by which the impurities can be removed from the final material, such assize exclusion chromatography, hydroxyapatite chromatography, reverse phase chromatography, ultrafiltration and fractionation by perchloric acid.

An example of size exclusion chromatography involves the following steps. The material, from which the impurities have to be removed, is reconstituted in 100 mM phosphate buffer, pH 7.2 (concentration–2.0 mg/ml). Ten milliliters of freshly reconstituted material is applied on a column (2.5 cm diameter×90 cm length) packed with Bio-Gel P30 (BioRad) and equilibrated with the same buffer. The chromatography is developed overnight at a flow rate of 20 ml/hour. The samples (4 ml) are collected and the final pool of material corresponding to low molecular weight proteins and peptides (>18K) is made according to SDS PAGE distribution.

An example, of hydroxyapatite chromatography involves the. following steps. The material, from which the impurities have to be removed, is reconstituted in 10 mM phosphate buffer, pH 6.5 (concentration–2.0 mg/ml). Ten milliliters of freshly reconstituted material is applied on a column (0.7 cm diameter×6 cm length) packed with Bio-Gel HTP (Bio-Rad) and equilibrated with the same buffer. The chromatography is developed at a flow rate of 0.25 ml/min. The column is washed with equilibrating buffer to remove all unbound material. Subsequently, the elution is performed with a linear gradient of phosphate buffer (10 mM to 500 mM). The samples (4 ml) are collected and the final pool of material corresponding to low molecular weight proteins and peptides (>18K) is made according to SDS PAGE distribution.

An example of reversed-phase High Performance Liquid Chromatography involves the following steps. The material, from which the impurities have to be removed, is reconstituted in 0.1% (v/v) of trifluoroacetic acid (TFA) at a concentration–2.0 mg/ml. Five milliliters of freshly reconstituted material is applied on a column (8 mm diameter×150 mm length) packed with 10 μm Nucleosil 100 C18 (Knauer) and equilibrated with 20% acetonitrile in 0.1% TAF. The chromatography is developed at a flow rate of 1.0 ml/min. The column is washed with equilibrating buffer to remove all unbound material. Subsequently, the elution is performed with 100% acetonitrile in 0.1% TFA. The samples (2 ml) are collected and the final pool of material corresponding to low molecular weight proteins and peptides (>18K) is made according to SDS PAGE distribution.

An example of perchloric acid fractionation involves the following steps. The material, from which the impurities have to be removed, is reconstituted in 10 mM phosphate buffer, pH 7.2 (concentration–2.0 mg/ml). Perchloric acid (0.45 M $HClO_4$) is added up to the concentration of 0.15 M and the mixture is stirred at room temperature for 1 hour. The resulting precipitate is removed by centrifugation and the supernatant, containing purified CLN is adjusted to pH 7.0 with 1 KOH and left overnight. The crystals of $KClO_4$ are removed by filter filtration and supernatant is dialyzed against water overnight. In another embodiment of the invention perchloric acid fractionation is use as a substitute of the ammonium sulphate precipitation step.

An example of ultrafiltration involves the following steps. The material, from which the impurities have to be removed, is reconstituted in 10 mM phosphate buffer, pH 7.2 (concentration–2.0 mg/ml). Ultrafiltration is carried out in Centricon Plus Ultracell PL-10 or Hollow fiber Amicon H1 P10-20 using standard ultrafiltration protocols.

As mentioned above, we have found that colostrum contains a proteinaceous fraction in the form of micelles. It has been observed that colostrinine can be recovered at higher yield when the raw colostrum is pre-treated with a micelle-breaking material, followed by a micelle-restoring agent, at various pH levels, prior to extraction with alcohol. Therefore, in an advantageous embodiment of the invention, the raw colostrum is pre-conditioned with a micelle-breaking material, which induces collapse of the micelles, then with a micelle-restoring agent, which is believed to disintegrate casein structures in colostrum, releasing more colostrinine peptides.

Preferably the micelle-breaking material is a calcium-chelating agent, such as EDTA (ethylene-diamine-N,N,N',N'-tetraacetic acid), which also binds $Mg^+$, or EGTA (ethylene glycol-O, —O'-bis(2-amino-ethyl)-N,N,N',N'-tetraacetic acid) with similar characteristics. The purpose of this is to release at least some of, preferably a majority of, the peptides entrapped between casein micelles.

The micelle-breaking material is preferably added in an amount to produce a solution that contains a concentration of micelle-breaking material in solution of 25-250 mM. The mixture is stirred and left to stand for a period of 10-30 minutes. The alcohol may be added immediately after addition of the micelle-dissolving material, or, in a more preferred embodiment, the addition of the micelle-breaking material is followed by addition of a micelle-restoring material, prior to the addition of the alcohol. The micelle-restoring material is preferably a source of $Ca^{2+}$ ions such as $CaCl_2$. The micelle-restoring material has the capacity to re-form micelles by providing calcium ions essential for micelle formation (recalcification).

In a preferred embodiment, the colostrum is conditioned to a pH from 5.5 to 8.0, more preferably 5.5-7.5 prior to the addition of the micelle-breaking material, the micelle-restoring material or the alcohol. Most preferably, the colostrum is conditioned to a pH from substantially 6.5-7.5. Still more preferably, the colostrum is conditioned to a pH from substantially 7.0 to 7.5, most preferably substantially 7.4. The pH conditioning may be achieved by addition of acid or alkali under the control of a pH meter.

A consistent pool of essentially IgG-free peptides can be isolated in a high yield using the method according to the invention. By simultaneously neutralising hydrophobic and ionic forces, we can obtain an optimum physiological combination of peptides. The yield of colostrinine peptides produced by extraction with methanol, according to the present invention, is generally around 500-600 mg per liter colostrum. Using pretreatment with EDTA and calcium chloride, the yield increased up to around 4000-5000 mg per liter colostrum. This compares with a prior art yield of around 200-300 mg per liter colostrum using the Janusz method described in WO98/14473.

The invention may be used in the separation from colostrum of any of the peptides known to be present in colostrum, specifically:

(i) the peptides disclosed in WO00/75173, i.e., LQTPQPLLQVMMEPQGD (SEQ ID 1); MPQNFYKLPQM (SEQ ID 2); VLEMKFPPPPQETVT (SEQ ID 3); LKPFPKLKVEVFPFP (SEQ ID 4); SEQP (SEQ ID 5); DKE (SEQ ID 6); DPPPPQS (SEQ ID 7); LNF (SEQ ID 8); VLPPNVG (SEQ ID 9); KYKLQPE (SEQ ID 10); SEEMP (SEQ ID 11); DSQPPV (SEQ ID 12); FPPPK (SEQ ID 13); WMEV (SEQ ID 14); DLEMPVLPVEPFPFV (SEQ ID 15); LFFFLPWNVLP (SEQ ID 16); MQPPPLP (SEQ ID 17); DQPPDVEKPDLQPFQVQS (SEQ ID 18); VYPFTGPIPN (SEQ ID 19); SLPQNILPL (SEQ ID 20); TQTPWVPPF (SEQ ID 21); LQPEIMGVPKVKETMVPK (SEQ ID 22); HKEMPFPKYPVEPFTESQ (SEQ ID 23); SLTLTDVEKLHLPLPLVQ (SEQ ID 24); SWMHQPP (SEQ ID 25); QPLPPTVMFP (SEQ ID 26); MHQPPQPLPPTVMFP (SEQ ID 27); PQSVLS (SEQ ID 28); LSQPKVLPVPQKAVPQRDMPIQ (SEQ ID 29); AFLLYQE (SEQ ID 30); FLLYQEPVLGPVR (SEQ ID 31); RGPFPILV (SEQ ID 32); or ATFNRYQDDHGEEILKSL (SEQ ID 33);

(ii) the peptides disclosed in WO02/46211, i.e., LVYPFTGPIPNSLPQNILP (SEQ. ID 34); MIWRLLQNEVPE (SEQ. ID 35); SLSQSKVLPV (SEQ. ID 36); LQTQTPW (SEQ. ID 37); EMPFPKY (SEQ. ID 38); PVEPFT (SEQ. ID 39); VPPFLQ (SEQ. ID 40); PMFLQ (SEQ. ID 41); EHMFV (SEQ. ID 42); TDRD (SEQ. ID 43); VQPT (SEQ. ID 44); PKVK (SEQ. ID 45); DDDE (SEQ ID 46); TEEV (SEQ ID 47); YQQE (SEQ. ID 48); FPPQ (SEQ. ID 49); GFGI (SEQ. ID 50); LQS (SEQ. ID 51); VW (SEQ. ID 52); GGK (SEQ. ID 53); DMV (SEQ. ID 54); ESQ (SEQ. ID 55); GRV (SEQ. ID 56); VEE (SEQ. ID 57); IGN (SEQ. ID 58); FFQ (SEQ. ID 59); RMF (SEQ. ID 60); FPP (SEQ. ID 61); MHH (SEQ. ID 62); NTE (SEQ. ID 63); and (iii) the nonapeptides disclosed in WO98/14473, i.e., VESYVPLFP (SEQ. ID 64).

Thus the invention may be used in processes to isolate any of the peptides identified by SEQ. ID 1-64, either individually, in a selected group, or all together.

The invention may be applied to any mammalian colostrum, although ovine, bovine or human colostrum are most commonly used. Furthermore, the invention has more general application beyond the separation of colostrinine peptides from colostrum. It is believed that the present invention has general applicability to the separation of small peptides from a mixture of the peptides with protein, lipids and other biological materials.

Furthermore, the starting point for the separation process according to the invention need not be colostrum as obtained directly from the mammal. It will be appreciated that the colostrum may be treated prior to being subjected to the separation method according to the invention, for example it may be defatted. Thus, the invention may be applied, with advantage to a derivative of colostrum, provided that the derivative still contains the colostrinine.

The method according to the invention may be applied, with advantage, to any body fluid, including cerebrospinal fluid, saliva, blood, ascitis or urine. The invention is particularly applicable to separations involving peptides in dairy fluids.

It will, therefore, be appreciated that the techniques described above may have wider application to the general separation of peptides from fluids containing higher molecular weight components including, but not limited to, proteins, lipids, carbohydrates and/or nucleic acids. In general, the fluid will be in the form of an aqueous liquid, having each of the peptides and other components either suspended in or dissolved in the liquid. Thus, according to another aspect of the present invention there is provided a method for recovering peptides from a fluid containing said peptides in combination with higher molecular weight materials, such as proteins, lipids, carbohydrates and/or nucleic acids, said method comprising: mixing the fluid with an alcohol to form an alcohol phase and a precipitate, the alcohol phase including the alcohol and at least some of the peptides, and the precipitate including at least some of the higher molecular weight materials; separating the alcohol phase from the precipitate; and recovering the alcohol phase.

References to % compositions herein relate to the percentage of the material in parts by weight, unless stated otherwise.

EXAMPLES

The invention will be further described with reference to the following examples.

Purification Protocols—For each comparative example, 10 ml of pooled colostrum was utilized. The colostrum was collected from sheep at different times postpartum and frozen until experiment. The protocol utilized in the following examples was identical, with the exception of initial conditioning of raw material either by pH or EDTA, as indicated below.

Example 1—10 m! of pooled raw colostrum (pH~6.5).

Example 2—10 ml of pooled raw colostrum (pH~6.5) conditioned with 25 mM EDTA, followed by addition of 50 mM $CaCl_2$ (recalcification).

Example 3—10 ml pooled colostrum conditioned at pH 7.4.

Example 4—10 ml pooled colostrum conditioned at pH 7.4 with 25 mM EDTA, followed by addition of 50 mM $CaCl_2$ (recalcification).

The same source of pooled raw colostrum (10 ml aliquots) was used to condition initial material at specific pH or EDTA/$CaCl_2$ treatment for 1 hour prior to addition of methanol. 100% methanol was added, up to a final concentration of 60% to each colostrum sample. The mixture was stirred for 30 minutes at room temperature, and was then centrifuged at 15,000 g. The supernatant was removed, and the alcohol allowed to evaporate from the supernatant in a dryer, until the volume of the supernatant was reduced to around 8.0 ml (this took around 30-60 minutes). An equal amount of saturated ammonium sulphate (100%) was added to the supernatant to obtain a final concentration of 50% ammonium sulfate. The supernatant/ammonium sulfate mixture was then rocked gently overnight at 4° C., allowing colostrinine peptides to precipitate. The preparation was centrifuged at 15,000 g to form a pellet, containing the colostrinine peptides. The pellet was dissolved in distilled water and dialyzed against 0.01 M PBS (phosphate buffered saline) overnight. The colostrinine peptides prepared by this method can be analysed in various tests and stored at −20° C.

Protein Recovery Assay—The protein concentration can be taken by reading the optical density of the solution at 280 nm prior to freezing. The protein recovery results are shown in Table 1, below.

TABLE 1

| Example | Sample | | |
|---|---|---|---|
| | OD 280 nm | Volume (ml) | Yield (mg) |
| 1- Raw Colostrum pH 6.5 | 0.83 | 2.0 | 1.66 |
| 2- Colostrum/EDTA/pH 6.5 | 0.86 | 2.0 | 1.72 |
| 3- Colostrum pH 7.4 | 3.97 | 2.0 | 7.94 |
| 4- Colostrum/EDTA/pH 7.4 | 9.44 | 2.0 | 18.88 |

The results indicate that protein recovery from the original 10 ml aliquots of colostrum is highly dependent on pH. These yields are higher than using the Janusz method and they are obtained using an easier and faster process.

Antigen Recognition Assay—The antigenic profile of the final material was determined by the ELISA method based on the antibodies prepared against nine synthetic peptides, for which sequences have been identified previously and are listed in Table 2.

TABLE 2

| Antigen Class | Sequence | Titer |
|---|---|---|
| A-1 | LQTPQPLLQVMMEPQGD | >25,600 |
| A-3 | VLEMKFPPPPQETVT | >25,600 |
| B-8 | DLEMPVLPVEPFPFV | >25,600 |
| B-9 | LFFFLPVVNVLP | >25,600 |
| C-2 | SLPQNILPL | >25,600 |
| C-11 | LSQPKVLPVPQKAVPQPDMPIQ | >25,600 |
| D-1 | ATFNRYQDDHGEEILKSL | >25,600 |
| LF | KCRRWEWRMKKLGAPSIPSITCVRRAF | >25,600 |
| IgG 2 | Whole molecule | 0 |

The antigen classes A, B, C and D are explained in WO00/75173. LF is a fragment of lactoferrin, having antibacterial property, IgG-2 antibody fragments serve as an indicator of colostrinine purity.

Briefly, 96 well ELISA plates were coated with samples of colostrinine recovered according to protocol 1-4 (approximately 10 micrograms of protein per 1 ml of 0.1 M bicarbonate buffer (pH 9.0). The plates were incubated at 37°C for 3 hours, washed with coupling buffer, and blocked with a standard solution of bovine serum albumin (BSA). 50 microliters of diluent BSA (0.75% solution) was pipetted into each well and 50 microliters of serum sample (Protein A purified rabbit antibody against specific antigen), diluted according to the initial titre, were added to column A of each row. 1:2 serial dilutions were made, moving down the plates. The plates were incubated, covered, for 60 minutes at room temperature, then washed 4 times with PBS solution. A volume of 50 microliters of goat anti-rabbit IgG-horseradish peroxidase conjugated antibodies (1:1000 dilution in BSA) was pipetted into each well and incubated for 60 minutes at room temperature. The plates were then washed 4 times with PBS wash solution and 50 microliters of substrate (2,2'-azino-bis3-ethylbenzothiazoline-6-sulphonic acid-diammonium salt) was added to each well, and incubated for 2 minutes at room temperature. The colorimetric reaction was stopped by adding 50 microliters of 1% SDS to each well, and the plates were read on a Dynatech plate reader (at 405 nm).

The results of these experiments (mean titres) are shown in Table 3 below. The values are in Units/ml×$10^3$. A Unit is defined as a final dilution for the recognition of antigen. It is clear that the recovery of individual peptides for which the final materials were tested (A-1; A-3; B-8; B-9; C-2; C-11; D-1; Lf and IgG-2) was highest for the extractions made at pH 7.4 (Experiment 3 and 4). In both cases the antigens were generally recognized to the highest dilutions tested.

TABLE 4-continued

Amino acid analysis of CLN

| Amino Acid | Colostrinin | | |
|---|---|---|---|
| | Original* | Original** | Novel*** |
| Leu | 11.04 | 11.27 | 10.47 |
| Phe | 4.38 | 4.42 | 4.77 |

*according to M. Janusz et al. ref. (FEBS LETTERS 1974, 49, 276-279)
**according to the average results obtained in further work using the Janusz et al. protocol
***according to the method according to the invention Biological assays: The potency of CLN produced according to this novel protocol has been tested in comparison with classical method and proved to be similar in the following activities: 1) reduction of 4HNE-protein adducts; 2) reduction of intracellular levels of ROS; 3) inhibition of 4HNE-mediated glutathione depletion; and 4) inhibition of 4HNE-induced activation of c-Jun NH2-terminal kinases.

SDS PAGE analysis. 1 D 15% pol acrylamide gel electrophoresis was carried out under reducing conditions. Staining with 1% Coomassie Blue shows striking similarities between final preparations of CLN obtained according to present invention and classical method.

Figure 1:
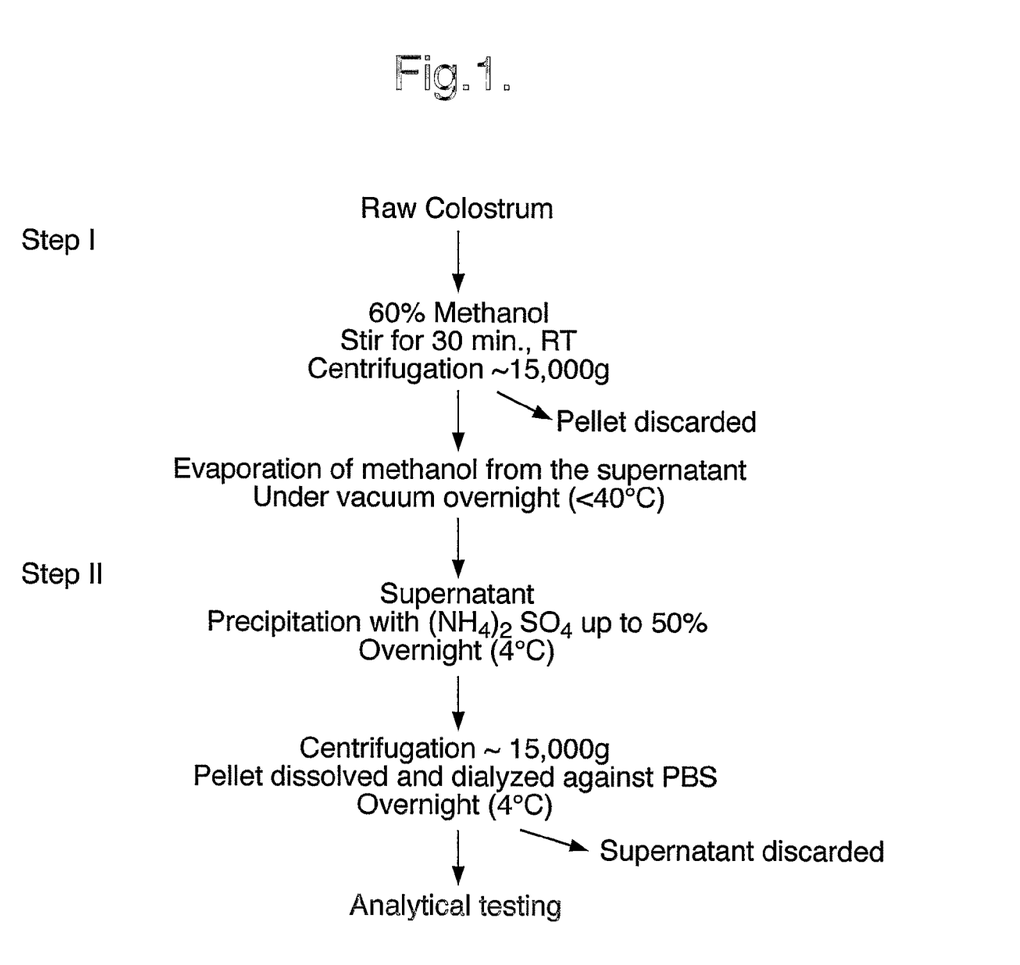
FIG. 1 is a chart summarising the extraction/purification protocol for colostrinine.
Figure 2:
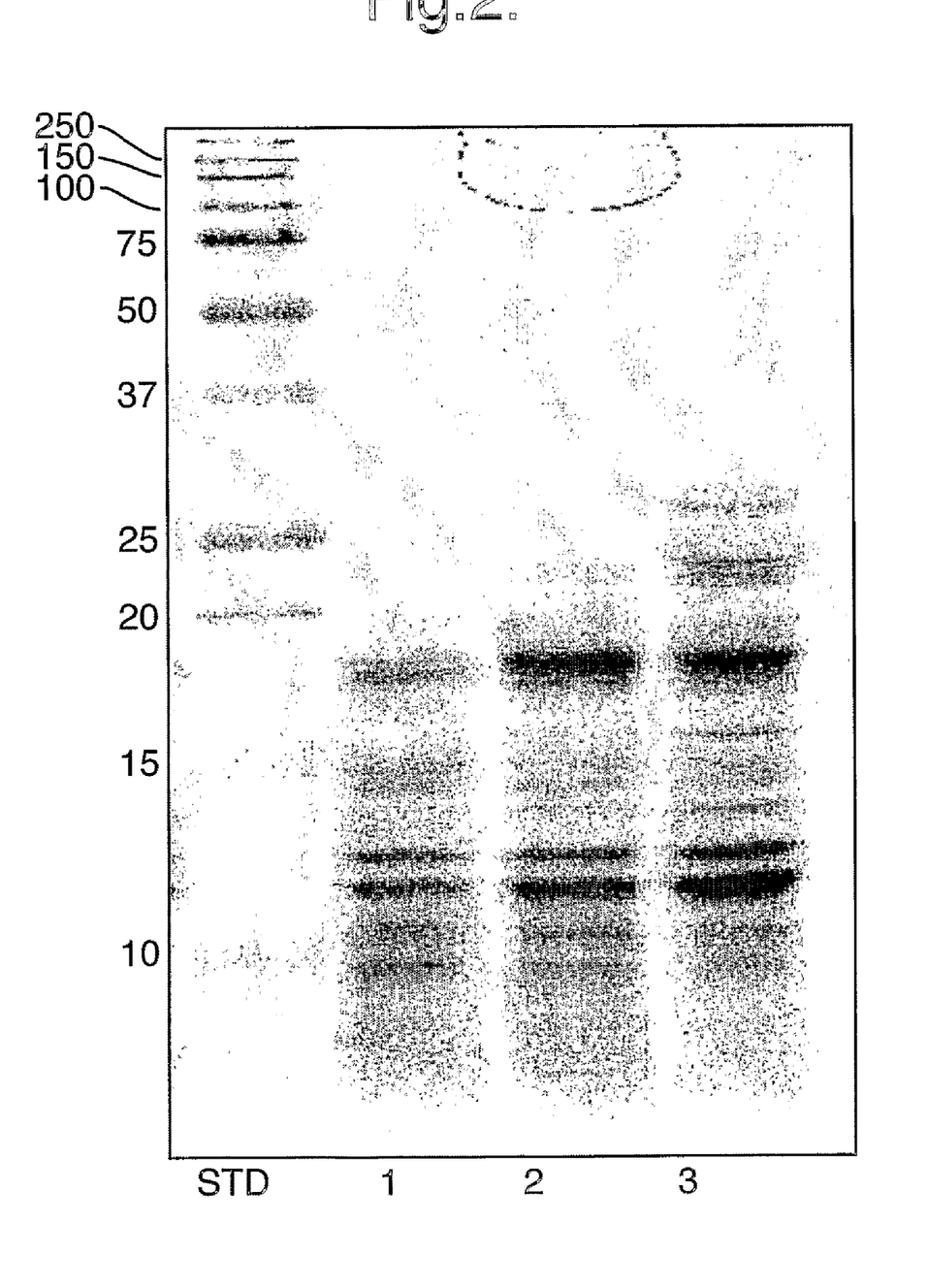
FIG. 2 shows the results of the SDS page analysis described below.

FIG. 2 shows the results of the SDS PAGE analysis. Samples were rehydrated, assayed for protein contents and

TABLE 3

| Experiment | A-1 | A-3 | B-8 | B-9 | C-2 | C-11 | D-1 | Lf | IgG-2 | Control | Experiment |
|---|---|---|---|---|---|---|---|---|---|---|---|
| 1 | 6400 | 6400 | 12800 | 6400 | 25600 | 25600 | 3200 | 1600 | 0 | 0 | 1 |
| 2 | 12800 | 12800 | 12800 | 6400 | 25600 | 25600 | 3200 | 6400 | 0 | 0 | 2 |
| 3 | 25600 | 12800 | 25600 | 25600 | 25600 | 25600 | 25600 | 25600 | 0 | 0 | 3 |
| 4 | 25600 | 25600 | 25600 | 25600 | 25600 | 25600 | 12800 | 12800 | 0 | 0 | 4 |

Amino acid analysis—The amino acid composition of colostrinine purified according to present invention confirms high content of proline (~20%) arid acidic amino acids. Table 4 shows high degree similarity in amino acid composition between colostrinine described previously and this present invention.

equal amount of protein was subjected to 1 D 15% gel SDS PAGE followed by staining with Coomassie Blue. In the drawing STD represents molecular weight markers; 1 represents colostrinine according to Janusz et al.; 2 represents colostrinine according to the present invention; and 3 represents colostrinine according to the present invention modified by EDTA/$CaCl_2$. As per SDS PAGE analyses, colostrinine obtained according to the present invention is substantially identical to the referenced material (Janusz method). Also the modification with EDTA/$CaCl_2$ provides similar material, although, there is an increase in higher molecular weight protein composition.

TABLE 4

Amino acid analysis of CLN

| Amino Acid | Colostrinin | | |
|---|---|---|---|
| | Original* | Original** | Novel*** |
| Asp/Asn | 3.42 | 3.05 | 2.80 |
| Ser | 5.66 | 5.70 | 5.05 |
| Glu/Gln | 15.48 | 15.29 | 15.77 |
| Gly | 3.15 | 3.13 | 3.03 |
| His | 2.54 | 2.45 | 2.14 |
| Arg | 2.32 | 2.45 | 3.34 |
| Thr | 5.73 | 5.69 | 5.30 |
| Ala | 2.78 | 2.99 | 2.13 |
| Pro | 21.07 | 20.92 | 22.50 |
| Tyr | 1.36 | 1.55 | 1.54 |
| Val | 9.27 | 10.34 | 11.10 |
| Met | 3.33 | 3.08 | 1.70 |
| Lys | 5.30 | 5.19 | 4.93 |
| Ile | 3.17 | 2.92 | 3.42 |

It will be appreciated that the invention may be modified. For example extraction agents other than alcohol may be utilized for the extraction. Some success has been achieved with ketones, such as acetone. Also, the ammonium sulphate precipitation step can be substituted with the perchloric acid fractionation as described previously. Whilst the starting point for the method is described as raw colostrum or defatted colostrum, it will be appreciated that other forms of colostrum or partially purified colostrum may be utilized as the starting point. For example, the method of the present invention could utilise and further purify colostrinine peptides that have previously been purified by the known prior art methods, such as the Janusz method.

The invention claimed is:

1. A method for recovering colostrinine peptides from a fluid, wherein the fluid comprises colostrum obtained directly from a mammal or mammalian colostrum that has been treated prior to the method provided the treated mammalian colostrum contains colostrinine peptides, said method comprising:
   mixing the fluid with an alcohol to form an alcohol phase and a precipitate, the alcohol phase including the alcohol and at least some of the colostrinine peptides to be recovered;
   separating the alcohol phase from the precipitate; and
   recovering colostrinine peptides from the alcohol phase.

2. The method according to claim 1, wherein the alcohol is methanol or ethanol.

3. The method according to claim 1, further comprising the step of removing at least some of the alcohol from the separated alcohol phase to leave a concentrated peptide phase, and recovering the colostrinine peptides from the concentrated peptide phase.

4. A method for recovering colostrinine peptides from a fluid, wherein the fluid comprises colostrum obtained directly from a mammal or mammalian colostrum that has been treated prior to the method provided the treated mammalian colostrum contained colostrinine peptides, said method comprising:
   mixing the fluid with an alcohol to form an alcohol phase and a precipitate, the alcohol phase including the alcohol and at least some of the colostrinine peptides to be recovered;
   separating the alcohol phase from the precipitate;
   recovering the alcohol phase;
   removing at least some of the alcohol from the recovered alcohol phase to leave a concentrated peptide phase;
   recovering the concentrated peptide phase; and
   dissolving a precipitation agent in the concentrated peptide phase to induce precipitation of at least some colostrinine peptides.

5. The method according to claim 4, wherein the precipitation agent is ammonium sulfate.

6. A method for recovering colostrinine peptides from a fluid, wherein the fluid comprises colostrum obtained directly from a mammal or mammalian colostrum that has been treated prior to the method provided the treated mammalian colostrum contains colostrinine peptides, said method comprising:
   adding EDTA to the fluid;
   mixing the fluid containing the added EDTA with an alcohol to form an alcohol phase and a precipitate, the alcohol phase including the alcohol and at least some of the colostrinine peptides to be recovered;
   separating the alcohol phase from the precipitate; and
   recovering colostrinine peptides from the alcohol phase.

7. A method for recovering colostrinine peptides from a fluid, wherein the fluid comprises colostrum obtained directly from a mammal or mammalian colostrum that has been treated prior to the method provided the treated mammalian colostrum contains colostrinine peptides, and wherein the fluid contains protein micelles to which the peptides are bound, said method comprising:
   adding a micelle-breaking material to the fluid, the micelle-breaking material being capable of inducing break up of the micelles in the fluid;
   mixing the fluid containing the added micelle-breaking material with an alcohol to form an alcohol phase and a precipitate, the alcohol phase including the alcohol and at least some of the colostrinine peptides to be recovered;
   separating the alcohol phase from the precipitate; and
   recovering colostrinine peptides from the alcohol phase.

8. The method according to claim 7, wherein the micelle-breaking material is EDTA or EGTA.

9. A method for recovering colostrinine peptides from a fluid, wherein the fluid comprises colostrum obtained directly from a mammal or mammalian colostrum that has been treated prior to the method provided the treated mammalian colostrum contains colostrinine peptides, said method comprising:
   adding $CaCl_2$ to the fluid;
   mixing the fluid containing the added $CaCl_2$ with an alcohol to form an alcohol phase and a precipitate, the alcohol phase including the alcohol and at least some of the colostrinine peptides to be recovered;
   separating the alcohol phase from the precipitate; and
   recovering colostrinine peptides from the alcohol phase.

10. The method according to claim 7, further comprising adding a micelle-restoring material to the fluid, prior to adding the alcohol, in order to re-form the protein micelles.

11. The method according to claim 10, wherein the micelle-restoring material is $CaCl_2$.

12. The method according to claim 1, wherein the fluid is preconditioned to a pH in the range 6.5-7.5 before adding the alcohol.

13. The method according to claim 1, wherein the alcohol added to the fluid is an amount sufficient to produce an alcohol concentration, based on the total volume of fluid, of from 40-80% (v/v).

14. The method according to claim 1, wherein the alcohol added to the fluid is an amount sufficient to produce an alcohol concentration, based on the total volume of fluid, of from 50-70% (v/v).

15. The method according to claim 1, wherein the alcohol added to the fluid is an amount sufficient to produce an alcohol concentration, based on the total volume of fluid, of from 55-65% (v/v).

16. The method according to claim 1, wherein the alcohol added to the fluid is substantially 100% pure.

17. A method for recovering colostrinine peptides from a fluid, wherein the fluid comprises colostrum obtained directly from a mammal or mammalian colostrum that has been treated prior to the method provided the treated mammalian colostrum contains colostrinine peptides, said method comprising:
   adding EDTA or EGTA to the fluid;
   adding $CaCl_2$ to the fluid containing the added EDTA or EGTA;

preconditioning the fluid containing the added EDTA or EGTA and the added CaCl$_2$ to a pH in the range of 6.5 to 7.5;

mixing the fluid containing the added EDTA or EGTA and the added CaCl$_2$ with an alcohol selected from the group consisting of methanol and ethanol to form an alcohol phase and a precipitate, wherein the alcohol is present in an amount sufficient to produce an alcohol concentration of from 40% to 80% (v/v), and wherein the alcohol phase includes the alcohol and at least some of the colostrinine peptides to be recovered;

separating the alcohol phase from the precipitate; and recovering peptides from the alcohol phase, wherein said recovered peptides comprise one or more peptides selected from

| | |
|---|---|
| LQTPQPLLQVMMEPQGD; | (SEQ ID 1) |
| MPQNFYKLPQM; | (SEQ ID 2) |
| VLEMKFPPPPQETVT; | (SEQ ID 3) |
| LKPFPKLKVEVFPFP; | (SEQ ID 4) |
| SEQP; | (SEQ ID 5) |
| DKE; | (SEQ ID 6) |
| DPPPPQS; | (SEQ ID 7) |
| LNF; | (SEQ ID 8) |
| VLPPNVG; | (SEQ ID 9) |
| KYKLQPE; | (SEQ ID 10) |
| SEEMP; | (SEQ ID 11) |
| DSQPPV; | (SEQ ID 12) |
| FPPPK; | (SEQ ID 13) |
| VVMEV; | (SEQ ID 14) |
| DLEMPVLPVEPFPFV; | (SEQ ID 15) |
| LFFFLPVVNVLP; | (SEQ ID 16) |
| MQPPPLP; | (SEQ ID 17) |
| DQPPDVEKPDLQPFQVQS; | (SEQ ID 18) |
| VYPFTGPIPN; | (SEQ ID 19) |
| SLPQNILPL; | (SEQ ID 20) |
| TQTPVVVPPF; | (SEQ ID 21) |
| LQPEIMGVPKVKETMVPK; | (SEQ ID 22) |
| HKEMPFPKYPVEPFTESQ; | (SEQ ID 23) |
| SLTLTDVEKLHLPLPLVQ; | (SEQ ID 24) |
| SWMHQPP; | (SEQ ID 25) |
| QPLPPTVMFP; | (SEQ ID 26) |
| MHQPPQPLPPTVMFP; | (SEQ ID 27) |
| PQSVLS; | (SEQ ID 28) |
| LSQPKVLPVPQKAVPQRDMPIQ; | (SEQ ID 29) |
| AFLLYQE; | (SEQ ID 30) |
| FLLYQEPVLGPVR; | (SEQ ID 31) |
| RGPFPILV; or | (SEQ ID 32) |
| ATFNRYQDDHGEEILKSL; | (SEQ ID 33) |
| LVYPFTGPIPNSLPQNILP; | (SEQ. ID 34) |
| MIVVRLLQNEVPE; | (SEQ. ID 35) |
| SLSQSKVLPV; | (SEQ. ID 36) |
| LQTQTPVV; | (SEQ. ID 37) |
| EMPFPKY; | (SEQ. ID 38) |
| PVEPFT; | (SEQ. ID 39) |
| VPPFLQ; | (SEQ. ID 40) |
| PMFLQ; | (SEQ. ID 41) |
| EHMFV; | (SEQ. ID 42) |
| TDRD; | (SEQ. ID 43) |
| VQPT; | (SEQ. ID 44) |
| PKVK; | (SEQ. ID 45) |
| DDDE; | (SEQ. ID 46) |
| TEEV; | (SEQ. ID 47) |
| YQQE; | (SEQ. ID 48) |
| FPPQ; | (SEQ. ID 49) |
| GFGI; | (SEQ. ID 50) |
| LQS; | (SEQ. ID 51) |
| VVV; | (SEQ. ID 52) |
| GGK; | (SEQ. ID 53) |
| DMV; | (SEQ. ID 54) |
| ESQ; | (SEQ. ID 55) |
| GRV; | (SEQ. ID 56) |
| VEE; | (SEQ. ID 57) |
| IGN; | (SEQ. ID 58) |
| FFQ; | (SEQ. ID 59) |
| RMF; | (SEQ. ID 60) |
| FPP; | (SEQ. ID 61) |
| MHH; | (SEQ. ID 62) |
| NTE; and | (SEQ. ID 63) |
| VESYVPLFP. | (SEQ. ID 64) |

18. The method according to claim 17 wherein ammonium sulfate is dissolved in the alcohol phase during the recovering step.

* * * * *